(12) United States Patent  
Rana et al.

(10) Patent No.: US 9,147,039 B2  
(45) Date of Patent: Sep. 29, 2015

(54) HYBRID QUERY SYSTEM FOR ELECTRONIC MEDICAL RECORDS

(75) Inventors: Sumit Rana, Verona, WI (US); Sagnik Bhattacharya, Madison, WI (US); Steven Ross Kappes, Verona, WI (US)

(73) Assignee: Epic Systems Corporation, Verona, WI (US)

( * ) Notice: Subject to any disclaimer, the term of this patent is extended or adjusted under 35 U.S.C. 154(b) by 203 days.

(21) Appl. No.: 13/231,461

(22) Filed: Sep. 13, 2011

(65) Prior Publication Data

US 2012/0066197 A1    Mar. 15, 2012

Related U.S. Application Data

(60) Provisional application No. 61/383,088, filed on Sep. 15, 2010.

(51) Int. Cl.
*G06F 7/00* (2006.01)
*G06F 17/30* (2006.01)
*G06F 19/00* (2011.01)

(52) U.S. Cl.
CPC .................................. *G06F 19/322* (2013.01)

(58) Field of Classification Search
CPC ............ G06F 19/322; G06F 17/30395; G06F 17/30398
USPC .......................... 707/706, 711, 736, 758, 770
See application file for complete search history.

(56) References Cited

U.S. PATENT DOCUMENTS

| | | | |
|---|---|---|---|
| 6,859,800 B1* | 2/2005 | Roche et al. ................... | 707/718 |
| 7,483,892 B1* | 1/2009 | Sommer et al. ......................... | 1/1 |
| 8,352,474 B2* | 1/2013 | Pickens et al. ................ | 707/741 |
| 8,375,014 B1* | 2/2013 | Brocato et al. ................ | 707/705 |
| 2002/0059161 A1* | 5/2002 | Li ..................................... | 707/1 |
| 2004/0049733 A1* | 3/2004 | Kerr et al. ..................... | 715/512 |
| 2004/0267722 A1* | 12/2004 | Larimore et al. ................. | 707/3 |
| 2007/0143149 A1 | 6/2007 | Buttner et al. | |
| 2008/0319962 A1* | 12/2008 | Riezler et al. ..................... | 707/4 |
| 2009/0089256 A1* | 4/2009 | Transier et al. ................... | 707/3 |
| 2011/0010195 A1* | 1/2011 | Cohn ................................ | 705/3 |

* cited by examiner

*Primary Examiner* — Md. I Uddin
(74) *Attorney, Agent, or Firm* — Boyle Fredrickson, S.C.

(57) ABSTRACT

An electronic medical record employs a hybrid search engine which can perform structured queries for comprehensive search results and text searches for rapid identification of relevant information. A standard structured database of medical data is rendered accessible to text searches by generating pseudo-documents from the database that can then be subjected to standard information retrieval pre-processing.

16 Claims, 8 Drawing Sheets

FIG. 7

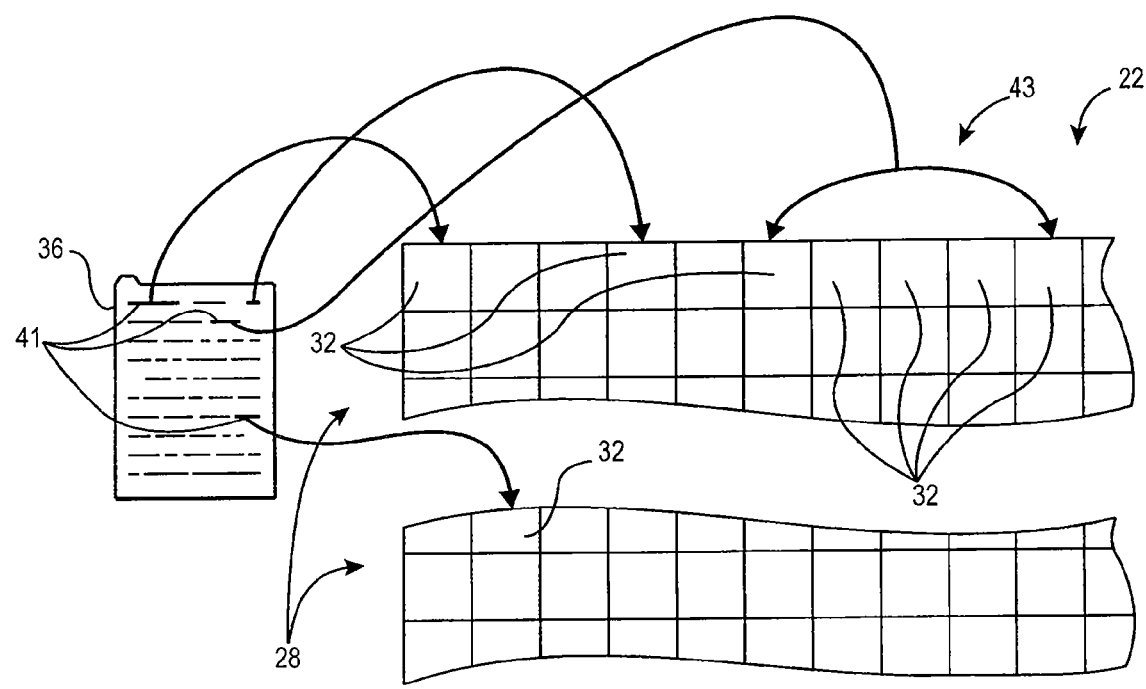
FIG. 13
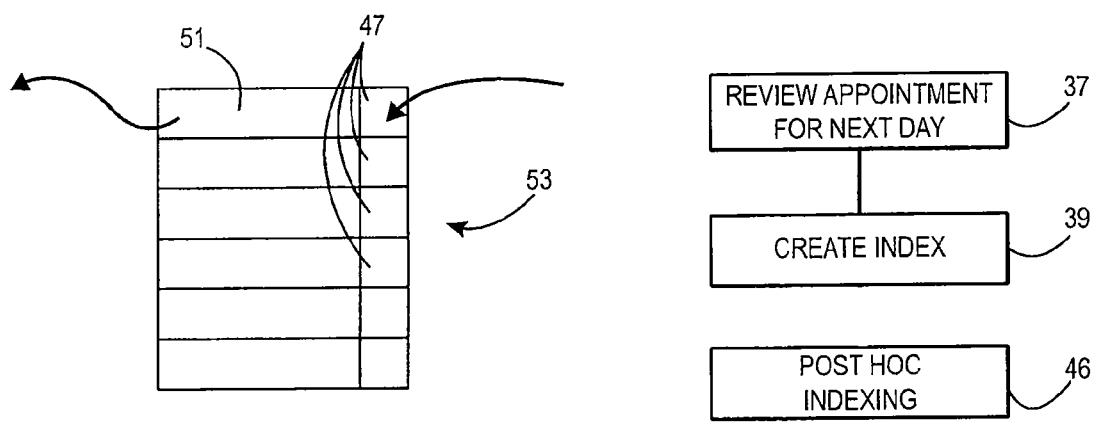
FIG. 14
FIG. 15

HYBRID QUERY SYSTEM FOR ELECTRONIC MEDICAL RECORDS

CROSS REFERENCE TO RELATED APPLICATION

This application claims the benefit of U.S. provisional application 61/383,088 filed Sep. 15, 2010 and hereby incorporated by reference.

BACKGROUND OF THE INVENTION

The present invention relates to electronic medical records used for storing clinically derived medical information about patients in a healthcare setting and in particular to an improved method of obtaining information from such electronic medical record systems.

Electronic medical record systems are computerized record-keeping systems intended to supplement or replace paper record systems in the healthcare environment. Such electronic medical record systems typically use a structured database holding a logical record for a given patient (for example, as may be represented as a row in a table) together with multiple data fields (for example, as may be represented as columns in the table). The values populating the data elements of the records and fields are collected by healthcare professionals to provide a comprehensive, reliable, and accurate view of the patient's health and medical treatment.

While such electronic medical record system databases often include text fields, for example, patient notes, their structured organization as a database ensures that the data of the database may be accessed in a deterministic manner to provide definitive information with respect to a given patient. For example, a review of an allergy report generated by a structured query of the structured database can be relied upon to provide an exhaustive, repeatable and comprehensive view of all the allergies of the patient contained in the structured database.

The structured organization also provides data that is readily machine readable (i.e. machine interpretable) because of the context information provided by the structure of the record fields and the known meaning of the fields. For example, the data of the structured database may be automatically reviewed by a computer (using a structured query) to accurately identify the allergies of a given population in the database, distinguishing, for example, "penicillin" as an allergy from "penicillin" as a treatment according to the record fields.

Such structured queries normally list data values together with record fields combined with Boolean operators and range operators.

The search of a structured database using a structured query search may be contrasted to "information retrieval" or text searches of a type familiar to users of search engines on the Internet. Such searches look for a text in text documents of largely unstructured text. The inherent imprecision in such searches is accommodated by presenting only a portion of the search results in ranked form according to statistical measurements. The results of a given search will vary over time as additional documents are added to the search space.

While such information retrieval searches can be extremely powerful, they are not comprehensive in the manner of a structured query of a structured database. For example, a search for the terms "osteoporosis" and "drugs" may yield useful information but cannot be relied upon to provide all or even the most relevant osteoporosis drug information. Further, because the text reviewed in a text search is normally not structured, the context or meaning of terms in the document may not be readily ascertained by the search engine. Thus, for example, a typical search intended to find drugs used for treatment of osteoporosis may also find drugs that exacerbate bone loss with use. Typically an information retrieval search cannot be considered exhaustive and some search terms may be disregarded as "noise" words and some relevant documents effectively discarded by low weighting.

The current promise of electronic medical record systems using structured databases is that they will substantially increase the efficiency and quality of healthcare by simplifying access to important medical data and providing a more comprehensive set of medical data. In this latter respect, the electronic medical record system can consolidate information collected by many different healthcare providers so that a physician, for example, has access not only to materials prepared by that physician but also information from other specialists, nurses, pharmacists and the like. Further, promised portability of the electronic medical records permits medical information collected about the patient to be preserved throughout the patient's life regardless of changes in physician or institution, offering greater longitudinal scope of medical information.

Current electronic medical record systems can produce a variety of useful reports that can present, compare, and even analyze data for ready access by a physician.

SUMMARY OF THE INVENTION

Paradoxically, the power and increased scope of the electronic medical record system can present an obstacle to providing quick access to information. Specifically, the complexity of the system may present an obstacle to a practicing physician who has little time to master or investigate a wide range of possible data reports that can be generated. Electronic medical record systems having increasingly large amounts of data on a patient may be subject to the "needle in a haystack" phenomenon where the wealth of data masks the particular data needed by a healthcare professional.

The present invention addresses this potential problem by providing a hybrid database access system using both conventional structured queries and text searches. While the latter searches are neither exhaustive nor rigorous, they can quickly provide relevant data to guide further searching, expose useful reports, and offer a quick overview of patient status.

In order to permit text searches of a structured database, the present invention creates a set of pseudo-documents from the data of the structured database. These pseudo-documents may then be "scraped" to generate an inverted index used in the text search. Usefully, the pseudo-documents may reflect actual standardized reports used in the structured database and relied upon by the medical community. In this way, the search results can be linked quickly back to a familiar report of the type generated by a standard structured query to provide additional information relevant to the search in a familiar organizational structure.

Specifically then, the present invention provides a hybrid electronic medical record system providing a structured database that can be accessed using a database management engine or a text search engine. The structured database provides a plurality of records associated with particular patients and provides clinically derived medical data separated into different identified data fields, and a database management engine communicates with the structured database and responds to structured queries to provide predefined reports collecting and organizing information from different fields of selected records according to the query. A document generator generates documents based on records associated with particular patients, and an inverted index indexes the documents according to text terms in the documents. The text search engine then communicates with the inverted index and responds to text queries to identify multiple ranked documents based on the indexing of the inverted index.

It is thus a feature of at least one embodiment of the invention to combine the certainty of a structured database necessary for medical decision-making with the rapid data access possible using a text search.

The document generator may further respond to a user selection of a ranked document to provide an associated predefined report via the database management engine.

It is thus a feature of at least one embodiment of the invention to eliminate the need to store documents used to create an inverted index and to ensure that the produced documents provide up-to-date medical information.

The associated predefined report may include text entry fields and the document generator may respond to data entry in the text entry fields by changing the medical data in the structured database.

It is thus a feature of at least one embodiment of the invention to return documents that function in a manner that is substantially identical to or analogous to a standard database-derived report which allows for modification of the database through data entry associated with the report, for example in text entry boxes.

The associated predefined report may include user-activatable links to structured queries to provide different predefined reports collecting and organizing information from different fields of selected records.

It is thus a feature of at least one embodiment of the invention to allow the user to identify data through sequential information retrieval searches and database structure searches providing linkage between reports generated by the database manager.

The database management engine may provide a user interface receiving user commands to execute predefined structured queries with the database management engine to generate predefined reports and wherein the document generator generates documents that duplicate the predefined reports.

It is thus a feature of at least one embodiment of the invention to provide a consistent data presentation independent of whether information retrieval or database queries are used to identify the presented data.

The document generator may generate documents based both on dynamic data from the structured database contained in the predefined reports and on static text data contained in the predefined reports.

It is thus an object of the invention to permit information retrieval searches that may be based on static text of a predefined report that is not derived from database data, for example form captions or headings titles.

The static text data is associated with text descriptions of the fields of the structured database from which the dynamic data of the predefined reports is obtained.

It is thus a feature of at least one embodiment of the invention to provide a method of converting structured data into text documents that fully captures context of the data implicit in the database organization.

The document generator may generate documents including chronological information describing a date of clinical observations of data of the predefined report recorded in the structured database at the time of generation of the documents.

It is thus a feature of at least one embodiment of the invention to permit the text search to be sensitive to the age of the medical data.

The document generator may generate documents including data from the structured database not in the predefined report but related to data used in the predefined report by structure of the database.

It is thus a feature of at least one embodiment of the invention to take advantage of the structure of data in a structured database to generate pseudo documents containing logically linked information.

The invention may further include a data entry interface allowing highlighting of data in the structured database as particularly significant for a text search and the document generator may generate documents including data indicating such highlights.

It is thus a feature of at least one embodiment of the invention to permit physician's flagging of data for future text searches.

The search engine provides a ranking based on term frequency of the query text.

It is thus a feature of at least one embodiment of the invention to permit an application of a standard text search technique to data in a structured database.

The search engine may provide a ranking based at least in part on the chronology of information associated with the dynamic data.

It is thus a feature of at least one embodiment of the invention to ensure the latest medical data is not supplanted by stale medical data in a text search context.

The search engine may further include a query expander processing medical words from the text query to add additional medical words corresponding to the medical words of the query. The additional text words may be, for example, synonyms or words related by co-morbidity or co-symptoms.

It is thus a feature of at least one embodiment of the invention to assist the user in preparing a broad scope search of a type difficult to perform using a standard structured query.

The system may include a heuristic monitor monitoring selection of ranked documents to provide a ranking based at least in part on historical selection of particular report types.

It is thus a feature of at least one embodiment of the invention to increase the relevance of search results by making use of search patterns of previous users.

The ranked documents may be represented by abstracts of the ranked documents generated at the time of a text query using a predefined abstract report collecting predefined information from the structured database.

It is thus a feature of at least one embodiment of the invention to provide improved summaries of documents because the documents are sourced from a structured database.

The system may include a text editor and in the selection of a ranked document may provide a predetermined data set to the text editor for the generation of a report.

It is thus an object of the invention to provide a simple method to assist physicians in collecting data from a structured database for the preparation of the report.

These particular objects and advantages may apply to only some embodiments falling within the claims and thus do not define the scope of the invention.

BRIEF DESCRIPTION OF FIGURES

FIG. 7 is a screenshot showing search results for a text search for the present invention;

FIG. 13 is a logical diagram showing the generation of a pseudo-document by pointers to database elements;

FIG. 14 is a figure of a data structure linking standard report numbers generated by the database to template information necessary to reconstruct the report with a standard query;

FIG. 15 is a flowchart showing the scheduling of indexing required by the present invention;

DETAILED DESCRIPTION OF THE PREFERRED EMBODIMENT

Hardware Description

Figure 1:
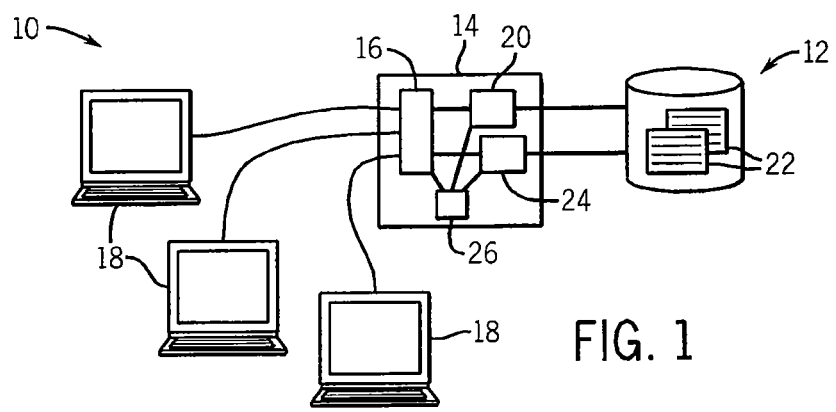
FIG. 1 is a simplified block diagram of an electronic medical record system suitable for use with the present invention providing both a structured query search and a text search of a structured database via multiple terminal accesses.

Referring now to FIG. 1, the electronic medical record system 10 per the present invention may include a data storage element 12, for example a disk array, communicating with an electronic computer 14. The electronic computer may execute an interface program 16 communicating with one or more terminals 18, for example, desktop computers including displays, keyboards and the like.

The interface program 16 may further communicate with a database program 20 providing standard database access to one or more database structured files 22 contained on the data storage element 12, for example, using a standard query language. In addition, the interface program 16 may communicate with a text search engine 24 that may perform a text search of the data in the structured files 22 as will be described.

The database program 20 and the text search engine 24 may communicate with a report interface 26 allowing rapid generation of reports using information from either.

Logical Operation

Figure 2:
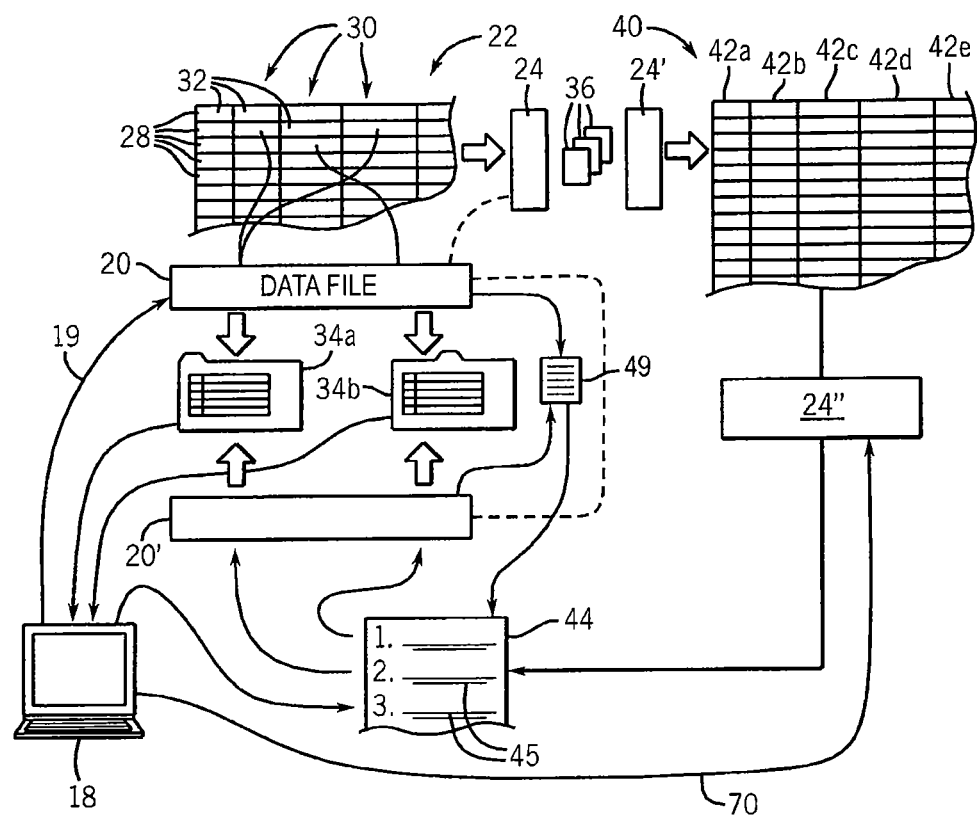
FIG. 2 is a process diagram showing the generation of pseudo-documents from the structured database of FIG. 1 for text searching and the linkage of the search results back to populated pseudo-documents.

Referring now to FIG. 2, the structured files 22 may, for example, provide a logical "flat file" having multiple records 28 each represented as a row. Each record 28 holds data elements 32 for multiple data fields 30 each represented as a column. The fields 30 will describe categories of medical information to provide context for the data elements 32. Examples of fields 30 include medical information such as allergies, prescriptions, height, weight, etc.; biographical information such as age and gender, and treatment history. The fields may also define certain text fields, for example, holding free text in the forms of sentences or paragraphs, for example, relating to patient notes. The values of the data elements 32 held in these fields 30 will normally derive from clinical observations by healthcare professionals. The values of the data elements 32 may be encoded, for example, through a mapping of text to particular numeric values and it will be understood henceforth that a reference to the value of the data elements 32 may indicate either the unencoded value or the encoded text.

It will be understood that generally each data element 32 must be interpreted (and hence obtains context) from the particular record 28 and field 30 in which it is found. Thus, for example, a data element 32, providing the name of a drug, may indicate that the drug is an allergen because the data element 32 is found in an allergen data field 30, and that the allergen is for a particular patient because the data element 32 is in a record 28 associated with that patient. The structure of the structured file 22 together with interpretive information in the database program 20 provides a structured database allowing information to be retrieved by field and record identification.

Generally any data element 32 in the structured database of the structured file 22 may be accessed through a structured query 19 describing a record or range of records and a field or range of fields and/or a Boolean combination of the same.

Normally, the data collected in response to a structured query 19 is presented in standard pre-prepared reports 34a and 34b presenting the data of the data elements 32 in a useful form. An example report 34 may be a listing of medical tests taken by a particular patient indicating the date and time of each test, the status of each test result, and the context of each test, for example, in an office visit. The data of the report 34 may be sorted according to date or any other field.

Generally the report 34 will include dynamic data collected from the structured file 22 by the standard query and also static data associated with the report 34 itself. Examples of static data may include text descriptions of the fields from which the dynamic data is obtained. Thus, for example, in the previously described report, a column providing test names which form dynamic data of the report 34 may be captioned with the phrase "test description", being static data of the report that does not change for this particular type of report even for different patients. The reports 34 may also include other information added to assist in interpretation of data presented such as a static text box, images, and graphics added by the person defining the report 34. The structured query 19 will typically be automatically invoked by a user requesting a particular report 34, for example, by clicking on a tab of the user interface or the like.

These reports 34a and 34b may be requested via a terminal 18 by a user who may review the reports 34 and use the data elements 32 in the reports 34 for clinical purposes, and may use the reports 34 themselves as templates to guide data entry into structured file 22. In this regard, the report 34 may include fields for text entry that may provide a mechanism for adding or changing elements 32 within the structured file 22. In these cases, a keystroke command or the like will invoke a database editing command that will take field and record information from the context of the record 34 and data from the field for text entry. In addition, the reports 34 may have "linking fields" allowing the viewer of the report to jump to other reports 34, for example, by invoking an embedded structured query 19. The above described operations and structure of the database program 20 comports generally with common database programs understood in the art.

Referring still to FIG. 2, generally, the structured file 22 may be accessed by a portion of the text search engine 24, typically as a background task, to generate an inverted index 40 necessary for an information retrieval search. This access may be performed, for example, at night or at other times of low usage and may access only a portion of the structured file 22 anticipated to be required as will be discussed further below.

Creation of the necessary inverted index 40 first generates multiple pseudo-documents 36. These pseudo-documents 36 are then processed by the text search engine 24' in a manner similar to that done by search engines that crawl the web. The result will generally be the search inverted index 40 listing words and linking them to addresses of different pseudo-documents 36. It will be understood that although pseudo-documents 36 are logically created as part of the indexing process, actual documents need not be constructed or retained but the data of those documents may be captured on the fly as will be described below.

A portion of the text search engine 24' may receive text queries 70 from a user terminal 18 and use the inverted index to identify a set of pseudo-documents 36. Document summaries 45 of a subset of these pseudo-documents may be returned in a ranked order in a display providing search results 44 and presented to the user on the terminal 18. Selecting individual document summaries 45 will, in the manner of a conventional Internet search engine, return an underlying document, which in the preferred embodiment is generated on the fly by a portion of the database program 20'. In a preferred embodiment, where the pseudo-documents 36 follow the same templates as the reports 34, the documents that are returned may be up to date reports 34 appropriate for the text query 70. These up-to-date reports 34 may have all the qualities of the standard report 34 including the ability to update or add information to the structured file 22 through the report 34 and the ability to link to other reports by "clicking" on link fields in the report.

As noted, in one embodiment, the pseudo-documents 36 may be in the form of reports 34 generated for particular patients and may include text derived both from the data elements 32 of the structured file 22 (dynamic text) and other text that would normally be found in the report (static text) such as that describing or elaborating on the data contained in the report 34. The portion of the text search engine 24' operates in a manner similar to a web crawler reviewing each of the pseudo-documents 36 to create the inverted index 40. This crawling process generally collects single words found in the pseudo-documents 36 (possibly excluding so-called "stop" or "noise" words) in a database of the inverted index 40. For example, the first column 42a of the inverted index 40 may identify a particular single word, for example, "diabetes". A second column 42b of the same record may provide identification of the particular pseudo-documents 36 in which the word "diabetes" is found and the location within the pseudo-document 36 (words number) and/or the field 30 in which the word is found. Other fields may include the storage of date and time associated with the clinical entry of the pseudo-document 36 (chronological information), for example as stored in a column 42c, as well as in data identifying the particular record 28 and fields 30 of the structured file 22 from which the word of the pseudo-document 36 was derived, as indicated by column 42d, and possibly a patient name in column 42e, typically being identical to the record number. This inverted index 40 permits a rapid response to text queries by pre-performing much of the searching process. Nevertheless, it will be understood that the inverted index 40 as described may be replaced with other types of structures or even a real-time search of the pseudo-documents 36.

The inverted index 40 then receives text searches from a portion of the text search engine 24', for example, requesting documents having particular words in them (e.g. "diabetes"). The query words are applied to column 42a to identify particular pseudo-documents 36 having each word of the query. The intersection of the set of documents identified for each query word may then, in one embodiment, be used to provide the pseudo-documents 36 that will be listed in the search results 44. Typically only a subset of the identified pseudo-documents 36 will be listed according to a ranking (as will be described). Each pseudo-document 36 in the document results will be identified by a short document summary 45. The document summaries 45 may be generated by the database program 20' using predefined abstract templates 49 associated with each of the reports 34 and, as will be described, provide a useful basis from which to generate patient notes by extracting critical report data.

Generally the search process of the text search engine 24' may be distinguished from the search process of the database program 20 by the fact that the latter is largely insensitive to the formal structure of the data as contained in the structured file 22 treating the data of the elements 32 as unstructured text. While both the text search engine 24 and the database program 20 may be used to obtain data from the structured file 22, the text search engine 24 may provide improved accessibility to data because it requires less understanding of the organization of the database. The text search engine 24 may also provide novel perspective on the data of the database because the results are not bound by preconceived report structures. For example, the database program 20 may be used to accurately search for whether a given patient has diabetes by generating a standard report of the patient's diseases. The text search engine 24 however will identify not only whether the patient has diabetes but also may simultaneously produce pseudo-documents 36 identifying drugs that can be counter-indicated for diabetics, other ailments to which diabetics are susceptible (co-morbidity) and other documents related to diabetes generally as will be described.

Referring now to FIGS. 2 and 15 the generation of pseudo-documents 36 and the index 40 by the text search engine 24 may be performed after hours or at other scheduled time removed from peak usage of the electronic medical record system 10. In one embodiment as indicated by process block 37, portions of the structured file 22 providing for appointment information may be reviewed and pseudo-documents only for patients having next day appointments (or appointments within a predetermined time range) will be generated or updated, significantly reducing the necessary size of the index 40 created as indicated by process block 39. Unexpected indexing requests (identified, for example, as relating to patients for whom entries in the index 40 have not been generated or updated) may be performed on the fly at the time of the search with suitable indication to the user of a possible delay as indicated by process block 46. Limiting the pseudo-documents 36 to standard reports for the patient may greatly accelerate this process.

Figure 4:
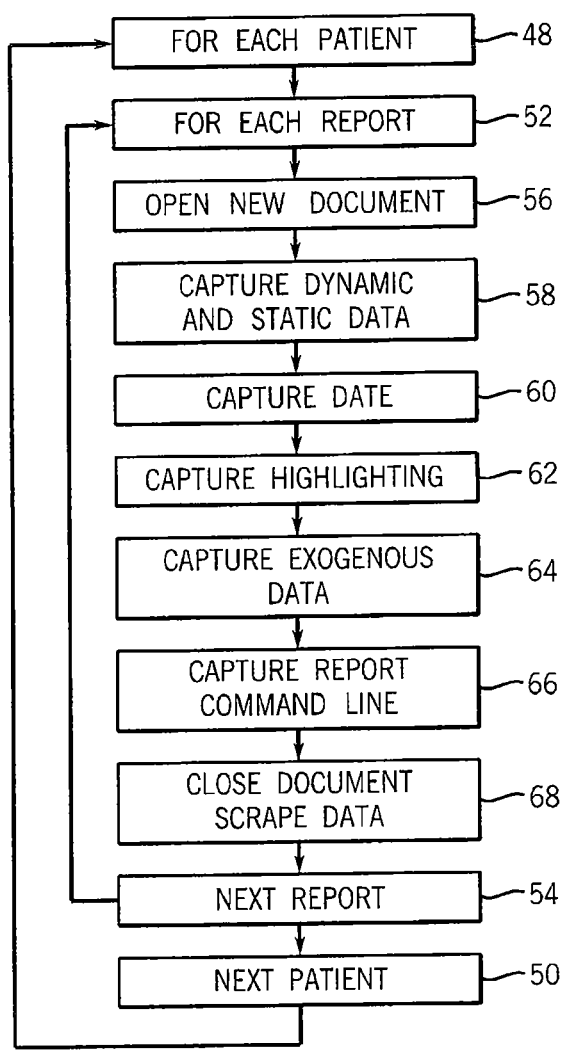
FIG. 4 is a flow chart of the steps of creating the pseudo-documents of FIG. 2.

Referring to FIG. 4, in the process of generating the pseudo-documents 36, the text search engine 24 executes a set of structured queries through the database program 20 reviewing data for each desired patient as indicated by the delimiters 48 and 50. In the above described embodiment in which the pseudo-documents 36 mirror standard reports 34 generated by the database program 20, the text search engine 24 may execute a nested set of structured queries generating each of the possible standard reports 34 for that patient as pseudo-documents 36 as indicated by delimiters 52 and 54. By using standard reports 34 as templates for the pseudo-documents 36, the accumulated wisdom embodied in the reports 34 can be used to inform the presentation of data and collection of data of the pseudo-documents 36. On the other hand, it will be recognized that these reports 34 may be augmented with other specially prepared reports used solely for the generation of pseudo-documents 36 or the pseudo-documents 36 may all be different than the reports 34 in structure and format.

Each pseudo-document 36 generated as a report by the database program 20 may then be converted to a text document by sequentially capturing, as indicated by succeeding process blocks 58 and 60, the dynamic and static text of that report and a regular reading order sequence (e.g. left to right, top to bottom). Table headers optionally may be inserted before the text of the data beneath that table header to increase the proximity of the two.

As noted above, as used herein the static data is data that is found only in the report and dynamic data is data derived from data elements 32 of the structured file 22. Thus, for example, table headings in a report are static data and data under those headings related to a patient will be dynamic data.

The present invention contemplates that certain data elements 32 may be highlighted by a physician as being particularly important in a text search. This highlighting may be accomplished as the physician reviews the data in a standard report 34 and the highlighting process essentially tags that data element 32 (for example by an additional field 42). In this case, at succeeding process block 62, the highlighted dynamic data is also marked in the pseudo-document 36 and this highlighting is preserved in the inverted index 40 to be used in a ranking process to be described.

As indicated by process block 64, the pseudo-document 36 may augment a standard report 34 by adding dynamic data not in the standard reports 34, for example, but found proximate to the data elements 32 of the dynamic data in the same record. Using this approach, each pseudo-document 36 can be assured to always include a patient name and, to the extent possible, each data element 32 will be associated by proximate chronological data indicating the date of the clinical observation or the like. This approach also may be used to ensure that other useful information, for example insurance carrier, physician, and healthcare institution, can be incorporated into each pseudo-document 36 so that text searches for these common limiting terms will provide the appropriate pseudo-documents 36.

At succeeding process block 66, the "command line" provides the data necessary to generate the pseudo-document 36 (essentially a template providing instructions for generating the pseudo-document much in the manner of generating a report 34 using structured queries). This command line data will be used by the database program 20' in reconstructing documents that are selected by the user from the search results 44. When the pseudo-documents 36 are identical to reports 34, this command line information may be as simple as an identification of a particular report 34 and its generating structured query 19.

As indicated by process block 68, at the conclusion of the generation of the pseudo-document 36, it is processed by a portion of the text search engine 24' to extract data for the inverted index 40 as has been described above. In one embodiment, the pseudo-documents 36 then may be destroyed.

Alternatively, referring to FIG. 13 the pseudo-documents 36 may be substantially a list of pointer values 41 identifying individual data elements 32 or ranges 43 of the structured file 22 in one or more records 28 that comprise a pseudo-document 36 which need not be human readable or even collected together in a continuous section of memory. The search engine 24 simply jumps to the necessary data in forming the index 40.

Figure 3:
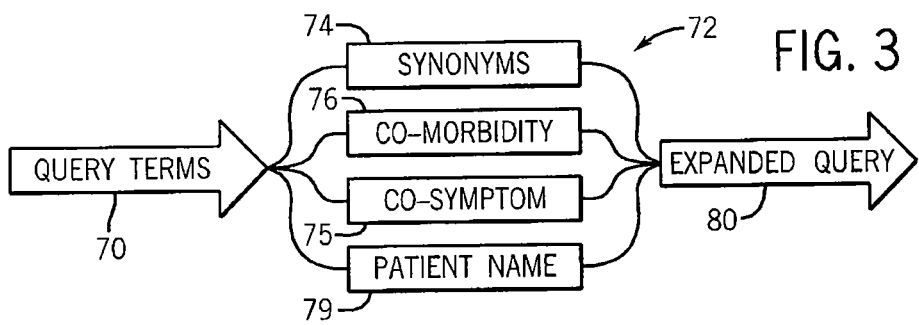
FIG. 3 is a flow diagram showing a query term expansion used in the text search of the present invention.

Referring now to FIGS. 2 and 3, a text query 70 consisting of one or more words possibly with logical and proximity-indicating connectors ("And", "Or", "Within N Words Of") may be provided to a portion of the text search engine 24'. The text search engine 24' in one embodiment may perform a query expansion 72 in which particular query words may be applied to a medical synonym dictionary 74 to obtain synonyms to help broaden the search coverage. Examples of such a synonym dictionary are the Unified Medical Language System (UMLS) metathesaurus sponsored by the United States National Library of Medicine http://www.nlm.nih.gov/pubs/factsheets/umlsmeta.html) and the controlled vocabulary Medical Subject Headings (MeSH®) from the United States National Library of Medicine (http://www.nlm.nih.gov/mesh/meshhome.html). In addition, a clinical terminology such as SNOMED CT® may provide for additional search terms linking the actual terms of the text query 70 to synonyms of the synonym dictionary 74 in a hierarchical fashion. A system like Soundex which is a phonetic algorithm for indexing names by sound may also be used to provide a more comprehensive search.

The hierarchical distance between the terms of the text query 70 and the synonyms of the synonym dictionary 74 may be used in calculating the ranking of the return documents with larger distances producing lower rankings for those terms.

Other expansions may include a co-morbidity table 76 that expands search terms indicating particular diseases to include terms for other diseases that tend to occur together with the particular search disease. Correspondingly, a co-symptom table 75 may provide search terms indicating symptoms that tend to appear with a given symptom term in the original query. Finally, implicit query terms, such as the name of the patient, a current date, etc. may be added as indicated by table 79. The result is an expanded search query 80 having additional terms and thus greater scope and scope informed by knowledge about the meaning of particular medical terms.

Figure 5:
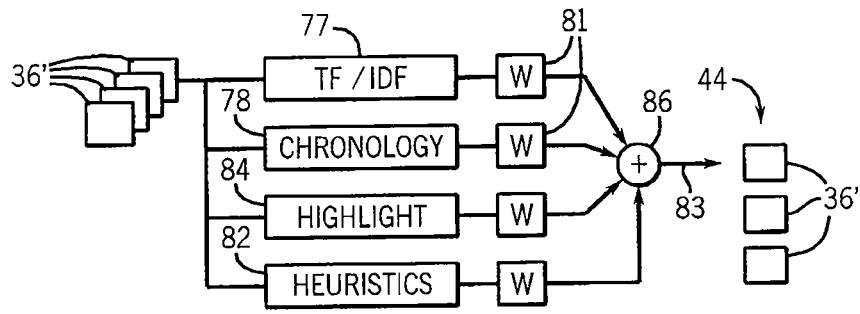
FIG. 5 is a block diagram showing a ranking system for the pseudo-documents collected in the text search of the present invention.

Referring now to FIGS. 2 and 5, as described above, the identified pseudo-documents 36' obtained via the text search engine 24' in response to a text query 70 must be ranked for display in the search results 44 which typically displays only a subset of the identified pseudo-documents 36. In one embodiment, this ranking produces a numeric ranking quantity by weighting different factors associated with the search pseudo-documents 36'. One such factor 77 can be the term frequency/inverse document frequency (TF-IDF) which provides a statistical measure proportional to the number of times a search term (query word) appears in a pseudo-document 36 offset by the frequency of the word in all of the pseudo-documents 36 extracted from the inverted index 40. This measure tends to identify significant query words and documents where the query words are highly represented (often normalized by the length of the document).

Another factor 78 determines how recently the data represented in the pseudo-document 36 was obtained from the chronology information embedded in the pseudo-document 36 as described above. Factor 84 reflects whether the given search term in the document was highlighted as described above with respect to process block 62 of FIG. 4. An additional heuristic factor 82 may consider whether the pseudo-document 36 is frequently selected in the search results 44 by either the given individual undertaking the search or by a group of individuals related to that individual. Separate heuristics may be collected depending on the individual's role in the health care setting (e.g. doctor, nurse etc.). Another factor can be the field 30 which the query 19 matches. For example, when the pseudo-document 36 is a patient note, as described below, the author name may get a higher ranking than the note text. Also, different pseudo-documents 36 may be considered more or less important by their type. For example a lab result pseudo-document 36 may be ranked as more significant than the patient note.

Each of these factors may be given a different weighting 81 determined empirically and then summed by summing block 86 to produce a single ranking value 83 which is associated with each pseudo-document 36' identified in the search and to provide a ranking order (e.g. greatest ranking value 83 listed first).

Figure 6:
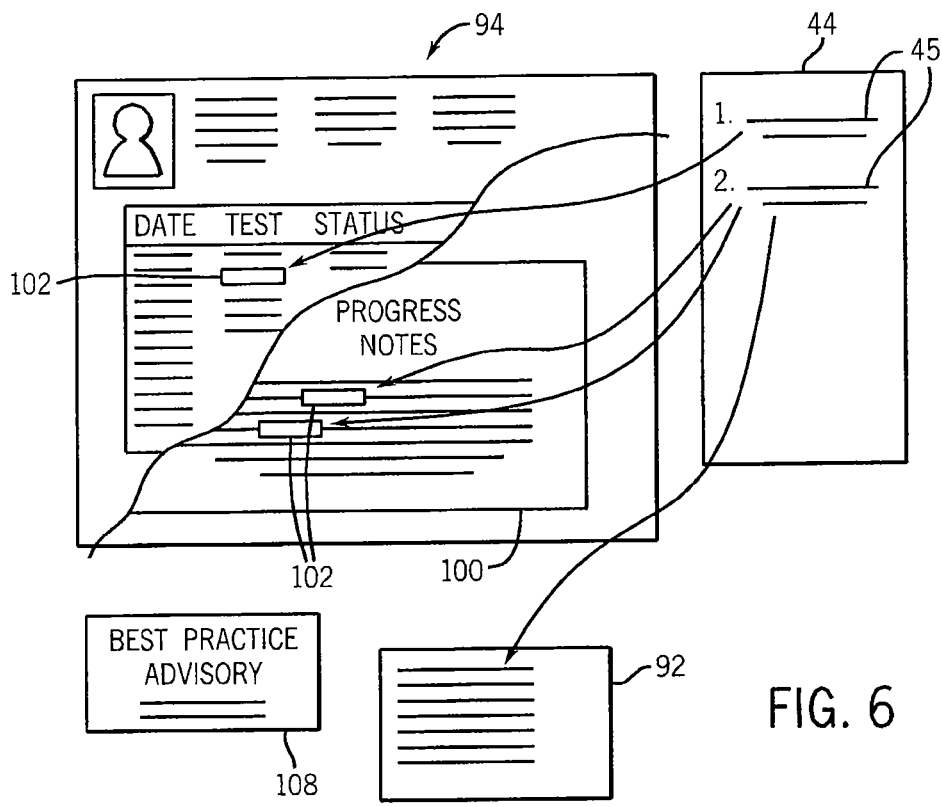
FIG. 6 is a process diagram showing a linking of retrieved pseudo-documents to populated search reports generated using a standard structured search query.

Referring now to FIG. 6, in an example search using the query term "diabetes", the text search engine 24 may augment this search term with the name of the patient, for example, taken from the context of the patient whose files are currently opened on the electronic medical record system. The query may be further expanded, for example, to include "lipid panel" as relevant to diabetic treatment and to include particular drugs, for example, Metformin (Glulcophage) per the query expansion process described with respect to FIG. 3.

The resulting expanded search query 80 may then be applied to the inverted index 40 to produce a listing of pseudo-documents 36 that can be ranked according to the ranking values 83 described above. The command line data from the inverted index may be used to identify a document summary 45 associated with each pseudo-document 36 that may be displayed in the search results 44. As described above, this document summary 45 not only may serve to provide a quick reference to the underlying pseudo-document 36 but also may serve as a mini report associated with the pseudo-document 36. For example, the pseudo-document 36 related to the lipid panel test may provide the results of that lipid panel in an abstract as follows:

lipid panel Jan. 11, 2009 (8 months)
cholesterol 192 HDL 39 LDL 123 triglycerides 160 VLDL 170

This document summary 45 provides a snapshot of the actual test and will typically, but need not, include data in the cited pseudo-document 36. Usefully, this document summary 45 may be dragged to an editing block 92 to expand it as follows:

lipid panel Jan. 11, 2009

| Component | Range | Value |
| --- | --- | --- |
| cholesterol: | –200 mg/dl | 192 |
| HDL: | 40-60 mg/dl | 39 |
| LDL: | 50-100 mg/dl | 123 |
| triglycerides: | 40-200 mg/dl | 160 |
| VLDL: | 5-40 | 170 |

This expansion may be done by creating two fields in the document summaries 45, one for display in the search results 44 and one for display in the editing block 92. The document summaries 45 may be generated by an additional template similar to and associated with the template for the reports 34 and may be applied to the structured file 22 by the text search engine 24.

Referring still to FIG. 6, selecting any document in the search results 44 (for example by clicking on its text representation) as indicated by arrows, will take the user to the referenced pseudo-document 36. For example, for the pseudo-document 36 related to the lipid panel test above, selecting that reference will take the user to a test result page 94 being a report generated using standard query terms for the particular patient. In contrast to the actual pseudo-document 36 whose data is enrolled in the inverted index 40, the generated test result page 94 will include the latest medical data in the structured file 22 to provide the user with complete and reliable data in contrast to a typical search engine which may produce stale data from stale documents which are indexed over a period of time. As will be described below, the present invention, by confirming that the inverted index is up-to-date ensures that the returned information is never stale. In certain cases, the pseudo-documents 36 will include text fields, for example, patient note 100. In this case, selecting that particular pseudo-document 36 will generate the underlying report showing patient note information and highlighting 102 the particular section of that document relied upon in returning the document as part of the query, for example the search terms, in a manner familiar to users of standard search engines on the web. The user may select multiple documents in the search results 44, and the underlying reports may be displayed concurrently in separate windows. This highlighting 102 may also be shown in the summaries 45 in the search results 44 as shown in FIG. 7.

Figure 7:
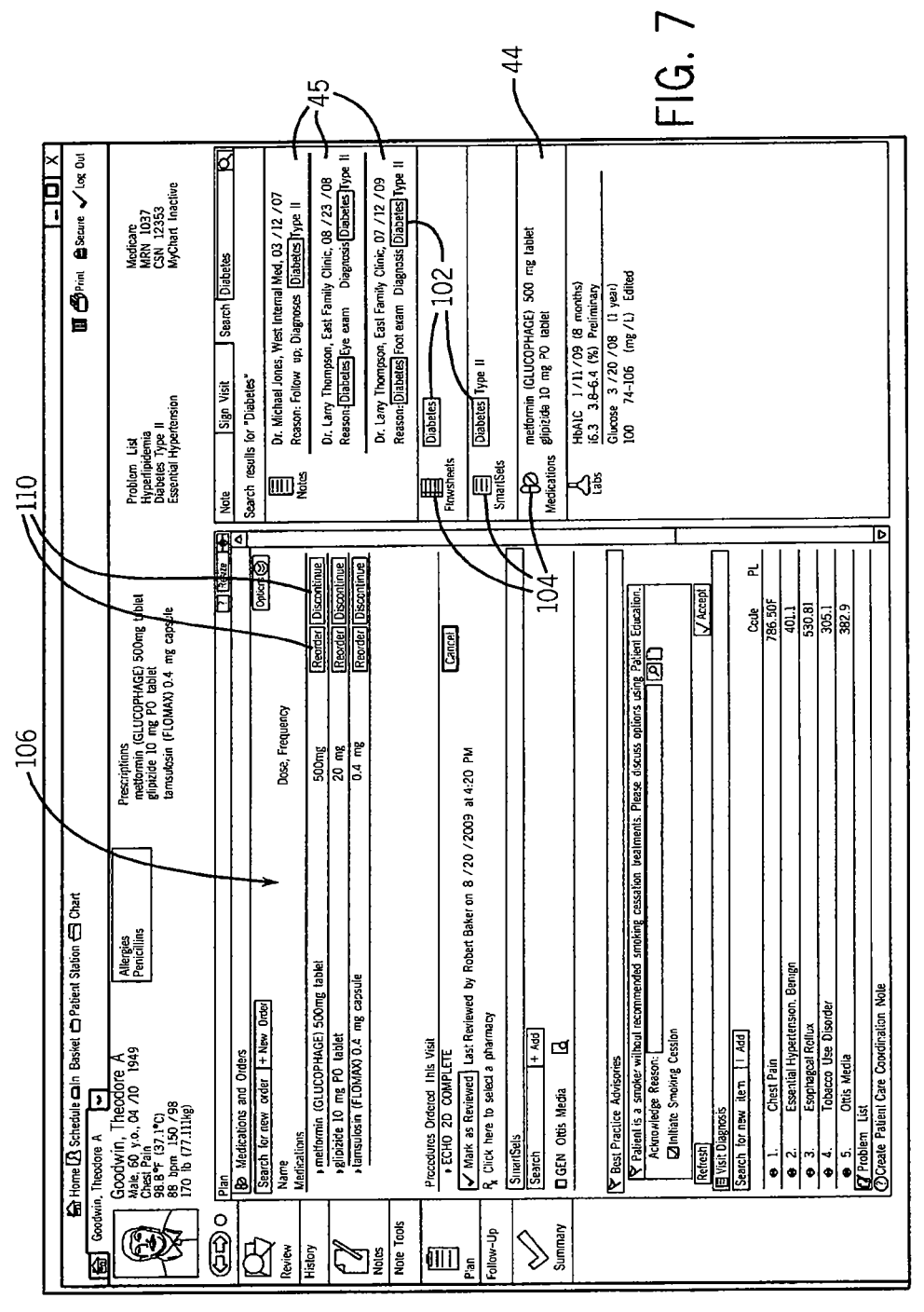

Referring now to FIG. 7, in an alternative embodiment, the search results 44 may arrange the pseudo-documents in terms of types of report 104 represented by the pseudo-documents 36. Thus, for example, pseudo-documents 36 that relate to patient notes may be separated from pseudo-documents that relate to lab tests, medications, and the like. In addition or alternatively, selecting a particular document summary 45 may produce a composite pseudo-document 106 combining portions of the underlying pseudo-documents 36, for example, for the topmost ranked pseudo-documents 36. This approach is consistent with the desire to create a more global view of the patient's medical data and can be obtained in a typical structured query 19.

The displayed pseudo-documents 36 and 106 may act exactly like reports generated using a structured query 19 so that, for example, reports including listings of medications provide the ability to reorder or discontinue those medications or otherwise change the underlying data by data entry controls 110. In addition, display of the pseudo-document 36 or 106 may be done in the same user interface normally used for structured query access to the structured file 22 so that the user may perform subsequent navigation through the patient record by using pre-established navigational tabs and links within the pseudo-documents 36 and within the user interface window.

Referring momentarily to FIG. 14, in one embodiment in which the pseudo-documents 36 are limited to the actual database reports 34 that may be generated by conventional operation of the database program 20, the document summaries 45 (shown in FIG. 2) may link to a report number 47 identifying a particular report 34 and enrolled in the index 40. Selecting a particular document summary 45 then invokes template information 51 and a translation table 53 links to the report number 47, the template information 51 including, for example, a structured query 19 and other information necessary to produce and display the report 34 exactly in the context that would be obtained in a conventional database search.

The invention may also search for conventional documents not necessarily in the structured file 22, for example, flow sheets describing steps taken to treat or evaluate particular conditions and these search results may return a flow sheet developed for the particular patient. As shown in FIG. 6, the query terms may also be used to trigger reminders and warnings 108, for example by auxiliary programs monitoring the query terms to trap the query terms and process them. These reminders and warnings can be expressed as pseudo-documents 36 even though they were not processed and incorporated into the inverted index 40. Reminders and warnings may also be used to adjust the ranking of documents and to highlight those documents that are relatively important based on independent analysis of the patient's records.

A certain number of "canned" pseudo-documents may also be created to permit the user to use the text search engine 24 to simply obtain information from the structured file 22 in an expedited manner. Thus, for example, a text search for a "lipid panel" may return the actual value of lipid panel test much in the same manner that some search engines will provide, for example, simple arithmetic operations without executing searches at all.

As used herein, the inverted index 40 may be any pre-processed index to the pseudo-documents 36 and need not have the logical structure of words and document addresses described above in a preferred embodiment.

Figure 16:
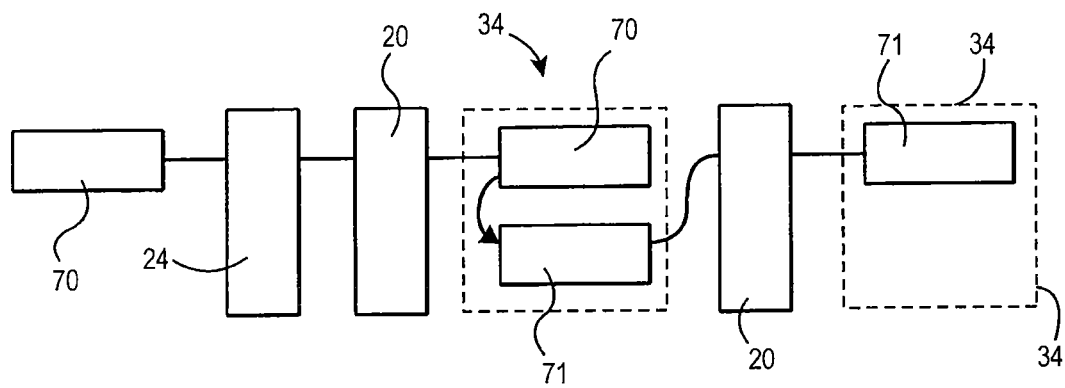
FIG. 16 is a flow diagram showing a user's navigation through information using successive information retrieval and database query type searches.

Referring now to FIG. 16, it will be appreciated that the present invention allows data to be obtained from the electronic medical record system 10 by a set of navigational steps that may include both information retrieval and database searching in a manner that is largely invisible to the user. Thus, for example, the user may enter a text query 70 that is processed by the text search engine 24 which is used to generate a search report 34 via the database program 20 including those terms of the text query 70 or a portion thereof. The resulting report 34, in fact generated by a database query through the database program 20, may allow other data 71 to be identified, essentially navigating from the results of the text query 70 to other data 71 based on the confines of the report 34. In the case where the other data 71 is a link to yet other reports 34, the database program 20 may be invoked again to produce yet another report 34 holding the other data 71.

Figure 17:
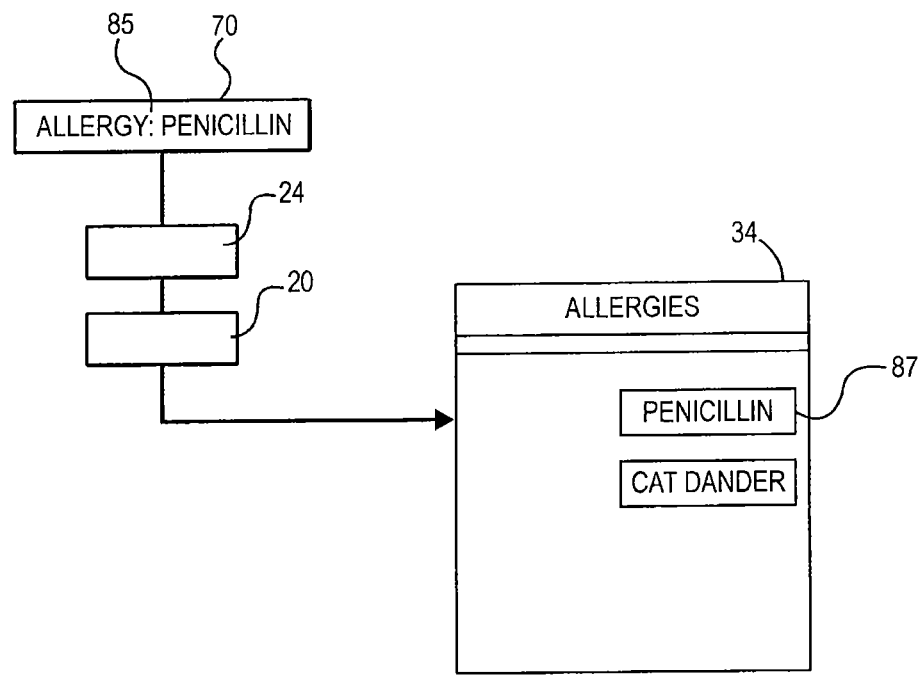
FIG. 17 is a flow diagram showing use of the information retrieval search to pre-populate forms for entry of data into the database.

Referring to FIG. 17, in one embodiment, the text query 70 may include a delimiter 85 (shown here as a colon) indicating that the following information is intended to be entered into the structured file 22. The search engine 24 may then process the remainder of the text query 70 exclusive of this data to be entered and may provide the latter to the database program 20 so that when the report 34 is generated the data to be entered is entered into a data entry field 87 in the report 34 pre-populating it for the convenience of the physician. In this way a very rapid location of the proper data entry form and entering of data may be obtained with a single information retrieval type search.

Example Implementation

Figure 8:
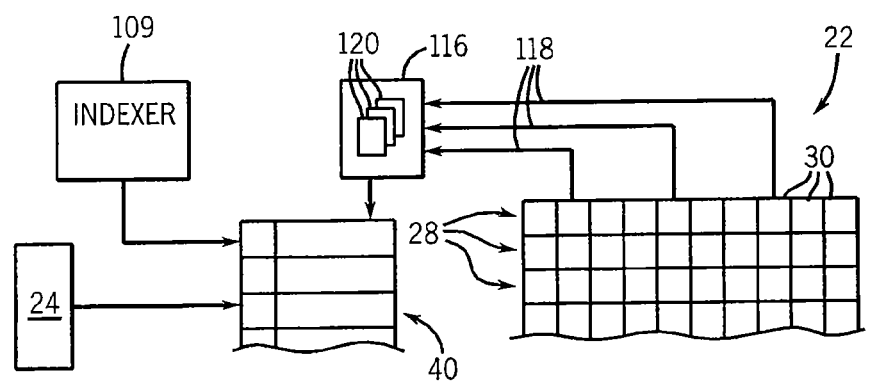
FIG. 8 is a process diagram similar to that of FIG. 2 showing an implementation eliminating the need for storage of the pseudo-documents.

Referring now to FIG. 8, in one implementation, the pseudo-documents 36, as described above may persist logically in the form of the index 40. In this embodiment, an indexer 109 may be triggered at certain times to produce the index 40 from the structured file 22 of the database.

Figure 9:
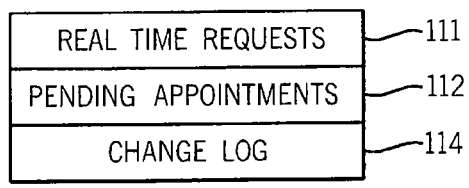
FIG. 9 is a scheduling chart showing prioritization of the indexing process.

Referring to FIG. 9, the indexing times may be prioritized to first perform indexing needed for current, real time requests for text searching by a text search engine 24 for a particular patient as indicated by schedule block 111. On a periodic basis, the next highest priority for the indexer 109 will be pending appointments for the immediate future as indicated by schedule block 112. This indexing for pending appointments ensures a current index for any anticipated text searches associated with pending patient visits. As indicated by schedule block 114, the lowest priority of indexing may be a background processing of changes in the structured file 22 that may have been recorded in a change log or the like to ensure that those changes are updated in the index 40.

In order to generate the index 40, a pseudo-document generator 116 may read particular fields 30 of the structured file 22, for example, for a single record 28 of a given patient. The particular records 28 for a given report may be identified by a report identification file 120. Data 118 from the particular fields 30 identified by the report identification file 120 are then indexed.

Figure 10:
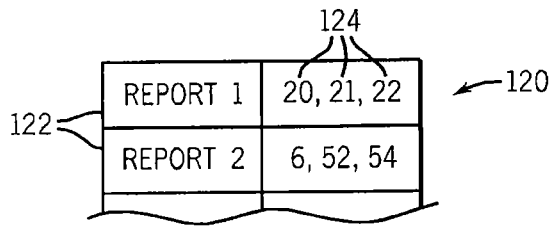
FIG. 10 is a fragmentary graphical representation of the report identification file used for generating pseudo-documents.
Figure 11:
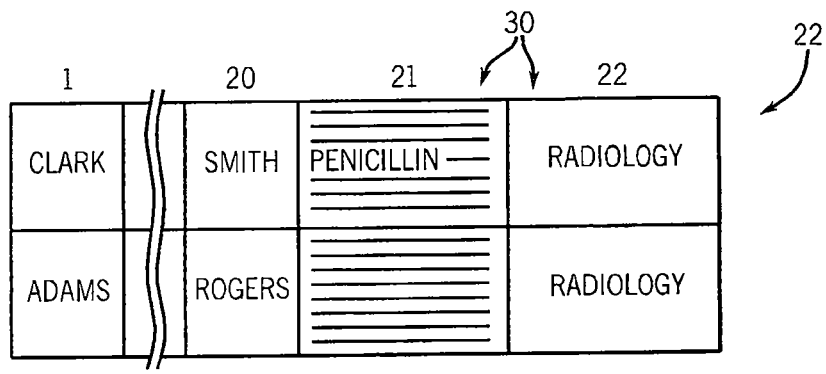
FIG. 11 is a fragmentary detail of the structured database showing the selected fields used for the generation of a pseudo-document.

Referring to FIG. 10, the report identification file 120 may identify particular report titles 122 (as will be used below) linked to fields 30 comprising that report. Referring to FIGS. 10 and 11, for example, a report having the title 122 of: "Report 1" may, for example, provide a pseudo-document 36 presenting a patient note, the patient note being a free text description by a doctor related to a particular patient. Report 1 may include, as depicted, fields 30 denoted 20, 21, and 22 of the structured file 22 representing the name of the physician, the text of the patient note and the department, respectively. The report identification file 120 links these fields together as if they were a free text document comprising the linked text in a particular order and proximity as in a single unitary document. Entries in a field 30 that are numerically encoded are decoded into text equivalents.

The pseudo-document 36 represented by a report can be considered to exist momentarily in the pseudo-document generator 116 for the purpose of indexing.

Figure 12:
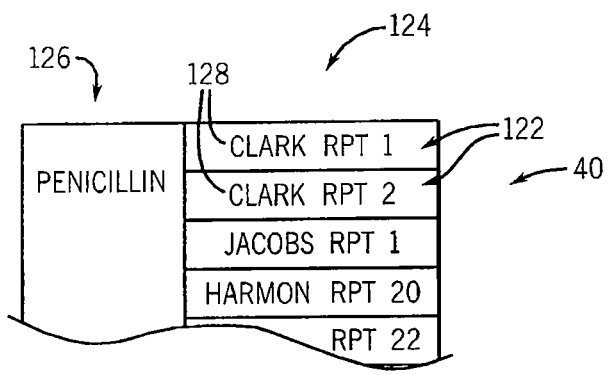
FIG. 12 is a fragmentary detail of the index produced by the process of FIG. 8.

Referring also to FIG. 12, the index 40 associates a given word with multiple reports where that given word is found. Thus, for example, the word "penicillin" in a word field 126 of the index 40 might be linked to numerous report titles 122 for different patients 128 in a report field 124.

Referring again to FIG. 8, the text search engine 24 in processing a text search may simply refer to the index 40, for example, creating a union of reports that have words in a query linking words by a logical "OR". The text search engine 24 may then generate search results using the report identification file 120 to return documents in real time. As a result, the returned documents will always present current data, even when the index 40 is not fully up-to-date. Further, it will be appreciated that separate storage of pseudo-documents 36 is not required but that the content of the pseudo-documents 36 may remain in the structured file 22.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What is claimed is:

1. A hybrid electronic medical record system comprising:
a structured database providing a plurality of records associated with particular patients and providing clinically derived medical data separated in different identified data fields; and
a medical record system computer processor configured to execute instructions loaded from a fixed memory to implement
  a database management engine communicating with the structured database and responding to structured queries to provide predefined reports collecting and organizing information from different fields of selected records according to the query;
  a document generator generating newly created pseudo-documents, where each newly created pseudo-document is based on a single record from the structured database that is associated with a particular patient, wherein the newly created pseudo-document is a predefined report that has been augmented by dynamic text and that is generated based on a single record and includes both static and dynamic text from the single record, the static text being inserted proximate to associated dynamic text;
  an inverted index indexing the newly created pseudo-documents according to text terms in the newly created documents; and
  a text search engine communicating with the inverted index and responding to text queries to identify multiple ranked newly created documents based on the indexing of the inverted index,
  wherein the search engine further includes a query expander processing medical words from the text query to add additional medical words corresponding to the medical words of the query,
  further wherein the additional medical words are words related by co-morbidity identifying medical words based on a co-morbidity table based on a recognized link between the query and the additional medical words.

2. The hybrid electronic medical record system of claim 1 wherein the document generator further responds to a user selection of a ranked document to provide an associated predefined report via the database management engine.

3. The hybrid electronic medical record system of claim 2 wherein the associated predefined report includes text entry fields and the document generator response to data entry in the text entry fields by changing the medical data in the structured database.

4. The hybrid electronic medical record system of claim 2 wherein the associated predefined report includes user-activatable links to structured queries to provide different predefined reports collecting and organizing information from different fields of selected records.

5. The hybrid electronic medical record system of claim 1 wherein the database management engine provides a user interface receiving user commands to execute predefined structured queries with the database management engine to generate predefined reports and wherein the document generator generates documents that duplicate the predefined reports.

6. The hybrid electronic medical record system of claim 5 wherein the document generator generates documents based both on dynamic data from the structured database contained in the predefined reports and on static text data contained in the predefined reports.

7. The hybrid electronic medical record system of claim 6 wherein the static text data is associated with text descriptions of the fields of the structured database from which the dynamic data of the predefined reports is obtained.

8. The hybrid electronic medical record system of claim 5 wherein the document generator generates documents including chronological information describing a date of clinical observations of data of the predefined report in the structured database at the time of generation of the documents.

9. The hybrid electronic medical record system of claim 5 wherein the document generator generates documents including data from the structured database not in the predefined report but related to data used in the predefined report by structure of the database.

10. The hybrid electronic medical record system of claim 1 wherein further including a data entry interface allowing highlighting of data in the structured database as particularly significant for an information retrieval search and wherein the document generator ranks documents at least in part according to whether the data of a documents is highlighted.

11. The hybrid electronic medical record system of claim 1 wherein the text search engine provides a ranking based on term frequency of the query text.

12. The hybrid electronic medical record system of claim 1 wherein the search engine provides a ranking based at least in part on chronology information associated with the text terms.

13. The hybrid electronic medical record system of claim 1 wherein the additional medical words are synonyms.

14. The hybrid electronic medical record system of claim 1 wherein the additional medical words are words related as co-symptoms.

15. The hybrid electronic medical record system of claim 1 wherein further including a heuristic monitor monitoring selection of ranked documents to provide a ranking based at least in part on historical selection of particular report types.

16. The hybrid electronic medical record system of claim 1 wherein the ranked documents are represented by abstracts of the ranked documents generated at a time of a text query using a predefined abstract report collecting predefined information from the structured database.

* * * * *